United States Patent
Nagao et al.

(10) Patent No.: US 8,124,825 B2
(45) Date of Patent: Feb. 28, 2012

(54) METHOD OF PURIFYING 2,7-DIMETHYLNAPHTHALENE

(75) Inventors: Shinichi Nagao, Okayama (JP); Hiroshi Ogawa, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 507 days.

(21) Appl. No.: 11/910,774

(22) PCT Filed: Apr. 6, 2006

(86) PCT No.: PCT/JP2006/307321

§ 371 (c)(1),
(2), (4) Date: Sep. 25, 2009

(87) PCT Pub. No.: WO2006/109667

PCT Pub. Date: Oct. 19, 2006

(65) Prior Publication Data

US 2010/0113853 A1    May 6, 2010

(30) Foreign Application Priority Data

Apr. 6, 2005  (JP) .................... 2005-109737

(51) Int. Cl.
*C07C 7/12*    (2006.01)

(52) U.S. Cl. .......... 585/828; 585/820; 585/822

(58) Field of Classification Search .......... None
See application file for complete search history.

(56) References Cited

U.S. PATENT DOCUMENTS

| 3,775,500 | A | 11/1973 | Thompson | |
|---|---|---|---|---|
| 6,057,487 | A * | 5/2000 | Munson et al. | 585/814 |
| 6,504,069 | B1 * | 1/2003 | Kyuuko et al. | 585/410 |
| 7,576,253 | B2 * | 8/2009 | Nagao et al. | 585/828 |

FOREIGN PATENT DOCUMENTS

| GB | 1333264 | 10/1973 |
|---|---|---|
| WO | WO 99/33770 | 7/1999 |

OTHER PUBLICATIONS

Supplementary European Search Report issued Nov. 5, 2008, in Application No. EP 06 73 1269.

* cited by examiner

*Primary Examiner* — Tam M Nguyen
(74) *Attorney, Agent, or Firm* — Antonelli, Terry, Stout & Kraus, LLP.

(57) ABSTRACT

To provide a method of purifying 2,7-dimethylnaphthalene comprising the step of bringing a raw oil containing a mixture of 1,7-dimethylnaphthalene and 2,7-dimethylnaphthalene together with a developing solvent into contact with L-type zeolite to thereby effect adsorption of 1,7-dimethylnaphthalene.

11 Claims, No Drawings

METHOD OF PURIFYING 2,7-DIMETHYLNAPHTHALENE

TECHNICAL FIELD

The present invention relates to a method of effectively separating 2,7-dimethylnaphthalene from stock oil containing a mixture of 1,7-dimethylnaphthalene and 2,7-dimethylnaphthalene, and particularly to a method of separating 2,7-dimethylnaphthalene, which cannot be readily isolated with high purity. 2,7-Naphthalene dicarboxylic acid prepared by oxidation of 2,7-dimethylnaphthalene and dimethyl 2,7-naphthalene dicarboxylate prepared by esterification of this acid are significantly useful as raw materials for high-quality polyesters having high thermal resistance and excellent physical strength.

BACKGROUND ART

Dimethylnaphthalene (hereinafter, referred to as "DMN") has ten isomers. In general, organic compounds are purified by operations such as distillation, crystallization, and adsorption and combinations thereof. Unfortunately, these dimethylnaphthalene isomers, which have significantly small differences in melting point and boiling point, cannot be readily purified by distillation or crystallization. Dimethylnaphthalene mixtures have been separated by conventional methods such as crystallization and adsorption.

For example, the following methods are known: Using ethyl alcohol as a solvent, 2,7-dimethylnaphthalene (hereinafter, referred to as "2,7-DMN") is selectively precipitated from a dimethylnaphthalene isomer mixture, and is separated by filtration while the DMNs having low melting points are present in a liquid state (refer to Patent Document 1); a DMN isomer mixture containing 2,7-DMN is treated with methanol and 2,7-DMN is isolated by crystallization (refer to Patent Document 2); high-purity 2,7-DMN is isolated from a stock oil containing DMN isomers by high-pressure crystallization (refer to Patent Document 3); and 2,7-DMN and 2,6-dimethylnaphthalene are separated from a DMN isomer mixture by high-selectivity adsorption with zeolite having ten-membered rings as an adsorbent (see Patent Document 4).

Unfortunately, no industrial method with low costs and a high yield through a simple procedure is established to isolate high-purity 2,7-dimethylnaphthalene from a dimethylnaphthalene mixture and particularly a mixture of 2,7-dimethylnaphthalene and 1,7-dimethylnaphthalene (hereinafter, referred to as "1,7-DMN").

Resin made of naphthalene dimethyl diester, as a polyester raw material, that is prepared by oxidation/esterification of dimethylnaphthalene containing these isomers exhibit poor physical and mechanical characteristics, such as low thermal resistance, low mechanical strength, and low dimensional stability. Thus, this cannot be used as a raw material for polyesters. Commercially available methods of separation of high-purity dimethylnaphthalene have been studied over a period of years.

[Patent Document 1] Japanese Unexamined Patent Application Publication No. 9-124520
[Patent Document 2] Japanese Unexamined Patent Application Publication No. 48-22448
[Patent Document 3] Japanese Unexamined Patent Application Publication No. 4-120027
[Patent Document 4] Japanese Unexamined Patent Application Publication No. 1-224336

DISCLOSURE OF THE INVENTION

An object of the present invention, for solving these issues, is to provide a method of making high-purity 2,7-dimethylnaphthalene from a dimethylnaphthalene isomer mixture in industrial scale with low production costs and a high yield.

The inventors have found that 2,7-dimethylnaphthalene, which is not adsorbed on a properly selected adsorbent, can be selectively separated from a stock oil containing both 1,7-dimethylnaphthalene and 2,7-dimethylnaphthalene by an adsorption process utilizing adsorptivity of the selected adsorbent to 1,7-dimethylnaphthalene, through extensive studies for solving the problems described above. In detail, the inventors have found that high-purity 2,7-dimethylnaphthalene can be separated by a combination of L zeolite as an adsorbent and an aliphatic or alicyclic hydrocarbon as a developing solvent and have accomplished the present invention.

Accordingly, the present invention provides a method of purifying 2,7-dimethylnaphthalene comprising bringing a stock oil containing a mixture of both 1,7-dimethylnaphthalene and 2,7-dimethylnaphthalene and a developing solvent into contact with L zeolite such that 1,7-dimethylnaphthalene is adsorbed on the L zeolite.

According to the present invention, high-purity 2,7-dimethylnaphthalene can be efficiently separated from a dimethylnaphthalene mixture containing 1,7-dimethylnaphthalene and 2,7-dimethylnaphthalene, with great industrial significance.

BEST MODE FOR CARRYING OUT THE INVENTION

A method of purifying 2,7-dimethylnaphthalene of the present invention comprises step (A) of bringing a stock oil containing a mixture of 1,7-dimethylnaphthalene and 2,7-dimethylnaphthalene and a developing solvent into contact with L zeolite to adsorb 1,7-dimethylnaphthalene on the L zeolite.

In the present invention, the stock oil containing a mixture of 1,7-dimethylnaphthalene and 2,7-dimethylnaphthalene before purification preferably contains 1,7-dimethylnaphthalene and 2,7-dimethylnaphthalene in a total amount of at least 70 weight percent. The method of making the stock oil containing the mixture of 1,7-dimethylnaphthalene and 2,7-dimethylnaphthalene is not limited. Preferably, the stock oil is produced by a stock oil production process (D) including steps (1) to (3). Step (1) is an alkenylation step that prepares 5-(p-tolyl)-2-pentene from p-xylene and 1,3-butadiene. Step (2) is a cyclization-dehydrogenation step that prepares 1,7-dimethylnaphthalene from 5-(p-tolyl)-2-pentene. Step (3) is an isomerization step that prepares 2,7-dimethylnaphthalene from 1,7-dimethylnaphthalene by isomerization. In the isomerization step (3), various isomerization processes can be employed. For example, use of a solid acid catalyst facilitates such isomerization.

Through the stock oil production process (D) including steps (1) to (3), a stock oil containing 1,7-dimethylnaphthalene and 2,7-dimethylnaphthalene in a total amount of at least 70 weight percent can be readily prepared.

An example of Step (1) is explained below.

Powdered zirconium oxide is added to an aqueous potassium hydroxide solution, followed by heating with stirring until zirconium oxide is wetted. The mixture was heated under reduced pressure to distill out water and then successively heated over night. After this drying stage, the mixture is calcined at an elevated temperature in air. The resulting catalyst is placed into a glass flask and is heated in a nitrogen atmosphere. After metallic sodium is added, stirring is continued at this temperature. p-Xylene is fed into the glass flask, followed by heating. With vigorous stirring, 1,3-butadiene is fed for a batch reaction. After the completion of the reaction, the mixture is cooled and is transferred into another glass container. After an aqueous sulfuric acid solution is supplied with stirring, the solution is left at rest. The clear supernatant liquid is supplied to a distillation column under reduced pressure to distill out low-boiling-point components. The bottom liquid is transferred into a distillation column for removing high-boiling point components and high-boiling point components are distilled out under further reduced pressure while 5-(p-tolyl)-2-pentene is distilled out.

An example of step (2) is explained below.

Deionized water is added to H mordenite, silica, and alumina sol containing alumina as a binder, followed by thorough mixing by stirring at room temperature. After the mixture was molded through an extruder, molded article is dried by heat and is then calcined at higher temperature to prepare a catalyst. This catalyst is packed into a cylindrical stainless-steel cyclization reactor, before 5-(p-tolyl)-2-pentene prepared in the step described above and nitrogen are fed into the reactor at elevated temperature under normal pressure. After the cyclization reaction, the reaction liquid is fed into a cylindrical stainless-steel dehydrogenation reactor filled with a platinum/activated charcoal catalyst. The system is heated for dehydrogenation reaction while heptane as a diluent is supplied. The reaction mixture is transferred into a reduced-pressure glass distillation column to recover heptane. The reaction solution after the removal of heptane is supplied to a reduced-pressure glass distillation column to separate low-boiling-point components and high-boiling-point components and to distill out 1,7-DMN with a purity of 98% from a middle plate of the distillation column.

An example of Step (3) is explained below.

H mordenite having an $SiO_2/Al_2O_3$ ratio of 203 and alumina sol are added to deionized water and are thoroughly mixed. After drying by heating, the mixture is further heated to be calcined in air. The calcined product is pulverized and particles with a diameter of 1.0 to 2.0 mm are collected as catalyst. The catalyst is packed into a cylindrical stainless-steel reactor. After 1,7-DMN is supplied from the bottom of the isomerization reactor, the reactor is heated under normal pressure to promote isomerization reaction. The weight ratio of 1,7-DMN to 2,7-DMN in the resulting reaction liquid is in the range of 2/3 to 1/1.

The stock oil containing the mixture of 1,7-DMN and 2,7-DMN is brought into contact with L zeolite, preferably, together with an organic developing solvent so that 1,7-DMN is selectively adsorbed on the L zeolite (adsorption step (A)).

Examples of the preferred developing solvent used in the present invention include linear and branched aliphatic hydrocarbons and alicyclic hydrocarbons having 6 to 14 carbon atoms, e.g. n-hexane, n-heptane, n-octane, isooctane, n-nonane, n-decane, n-undecane, n-dodecane, cyclohexane, decalin, and methylcyclohexane. Among these preferred are substances having boiling points that are significantly different from that of 2,7-dimethylnaphthalene because the use of such developing solvent can be separated by distillation later.

These aliphatic hydrocarbons or alicyclic hydrocarbons may be used alone or as a mixture. The aliphatic hydrocarbons and alicyclic hydrocarbons may be used in combination.

The L zeolite used in the present invention has a $SiO_2/Al_2O_3$ ratio (molar ratio) of 5.2 to 7.0 and preferably 5.6 to 7.0. Preferably, the zeolite has one-dimensional pores having a diameter of 0.7 nm (12-membered oxygen ring) and three-dimensional pore paths. An example of L zeolite is KL zeolite. A commercially available KL zeolite is "HS-500" ($SiO_2/Al_2O_3$ ratio (molar ratio)=6.0) made by Wako Pure Chemical Industries, Ltd.

In addition to the KL type, another example of L zeolite is KL zeolite which is substituted by at least one metal ion selected from alkali metal ions and alkaline earth metal ions, for example, ions of sodium, lithium, rubidium, cesium, barium, calcium, magnesium, strontium, and lanthanum. These zeolites may be used without processing or after steam treatment, alkali treatment, acid treatment or ion exchange treatment. Preferably, the zeolite should be shaped into spheres, noodles, and cylinders.

The method of contact of the stock oil and the developing solvent with the L zeolite is not limited. Preferred methods in the present invention include letting the stock oil through an adsorption layer filled with the L zeolite while letting the developing solvent through the layer; and premixing the stock oil with the developing solvent and letting the mixture through the adsorption layer.

The amount on the basis of weight of the developing solvent to the total amount of dimethylnaphthalenes in the stock oil is 1 to 200 times, preferably 5 to 150 times, and more preferably 10 to 100 times. The preferred amount of the solution (total of the stock oil and the developing solvent) fed to the adsorption layer is in the range of 0.1 to $10.0\,h^{-1}$ on the basis of liquid hourly space velocity (LHSV) to the adsorption layer. The preferred temperature of the adsorption layer during the liquid flow is in the range of 10 to 200° C. and more preferably 20 to 150° C.

Such adsorption operation enables 1,7-dimethylnaphthalene to be selectively adsorbed and a solution primarily containing 2,7-dimethylnaphthalene and the developing solvent to flow through. From this recovered solution, the developing solvent is separated by, for example, distillation to isolate high-purity 2,7-dimethylnaphthalene (developing solvent separation step (C)).

In general, desorption and/or recovery of an adsorbed target substance requires complicated operations and strict control of conditions. However, in the present invention, the target substance, 2,7-dimethylnaphthalene, can be isolated through a simple process because the target substance is not adsorbed.

Desorption solvents are used in order to separate or recover dimethylnaphthalenes (mainly 1,7-dimethylnaphthalene) desorbed on the zeolite by desorption after the adsorption operation (adsorption step (A)). In the present invention, preferred are aromatic hydrocarbons, such as benzene, toluene, o-xylene, p-xylene, m-xylene, ethylbenzene, and diethylbenzene in view of, for example, desorption time. The preferred amount on the desorption solvent is in the range of 1 to 200 times on the basis of weight to the total amount of dimethylnaphthalenes in the stock oil. The preferred amount of the solution fed to the adsorption layer is in the range of 0.05 to $20.0\,h^{-1}$ on the basis of LHSV. The preferred temperature of the adsorption layer during the liquid flow is in the range of 10 to 200° C. and more preferably 20 to 150° C. The recovered 1,7-dimethylnaphthalene can be recycled as a raw material in the isomerization step (3).

The adsorption step (A) and the desorption step (B) in the present invention may be in any form of batch, flow, and semi-batch, through a fixed bed, fluid bed, or moving bed, for example. From the industrial viewpoint, these steps should preferably be carried out by a known pseudo moving bed process (see, for example, Japanese Unexamined Patent Application Publication No. 8-217700).

EXAMPLES

The present invention is now explained in more detail by Examples, but is not limited to these Examples. In Examples and Comparative Examples, raw materials and target substances were analyzed by gas chromatography. Hereinafter, "part(s)" denotes part(s) by weight.

Synthetic Example 1

Alkenylation Step for Preparation of 5-(p-tolyl)-2-pentene from P-Xylene and 1,3-butadiene (Step (1))

Powdered zirconium oxide (30 parts) was added to an aqueous solution containing potassium hydroxide (5 parts) and was impregnated with stirring at 50° C. for 1 hour. Water was distilled out at 70° C. under reduced pressure. After the residue was dried at 115° C. over night, and it was calcined at 500° C. in air. The resulting catalyst (10 parts) was fed to a glass flask and was stirred at 180° C. in a nitrogen atmosphere. After metallic sodium (0.5 parts) was added, the mixture was stirred for 60 minutes at this temperature. p-Xylene (1000 parts) was fed into the glass flask, and the mixture was heated to 140° C. With vigorous stirring, 1,3-butadiene (70 parts) was supplied by spending one hour to perform a batch reaction. After the completion of the reaction, the solution was cooled and transferred into another glass vessel. With stirring, an aqueous 10% sulfuric acid solution (50 parts) was fed and the solution was allowed to stand. The yield of 5-(p-tolyl)-2-pentene to the reactant p-xylene was 82%. The clear supernatant liquid was supplied to a 23-kPa distillation column at a feeding rate of 63 parts/hr to remove low-boiling-point components. The bottom liquid was transferred into a 5-kPa distillation column for removing high-boiling-point components, 5-(p-tolyl)-2-pentene was isolated at a rate of 10 parts/hr while the high-boiling-point components were removed at a rate of 2 parts/hr.

Cyclization-Dehydrogenation Step for Preparation of 1,7-dimethylnaphthalene from 5-(p-tolyl)-2-pentene (Step (2))

Deionized water (500 parts) was added to H mordenite (15 parts) made by Tosoh Corporation, silica (270 parts), and alumina sol (21 parts) containing 70 weight percent alumina as a binder, and the mixture was thoroughly stirred at room temperature. After shaping of the slurry with an extruder, the shaped article was dried at 110° C. and then calcined at 350° C. for 3 hours to prepare a catalyst. After this catalyst was packed into a cylindrical stainless-steel cyclization reactor, 5-(p-tolyl)-2-pentene prepared by the preceding step was fed at a rate of 10 parts/hr while nitrogen was fed at a rate of 250 parts/min to complete a cyclization reaction at a temperature of 170° C. under normal pressure. The molar ratio of the diluent solvent to the raw material was 11. After the cyclization reaction, the reaction solution was fed to a cylindrical stainless-steel dehydrogenation reactor filled with 40 parts of 1%-platinum/activated charcoal catalyst (made by N.E. CHEMCAT). The reaction temperature was 280° C. During the dehydrogenation reaction, n-heptane as the diluent solvent was also fed at a rate of 20 parts/hr. After the reaction, the solution was fed to a glass distillation column under a reduced pressure of 19 kPa to recover n-heptane. The residual reaction solution after the removal of n-heptane was fed to a glass distillation column under a reduced pressure of 13 kPa to separate low-boiling-point components at a rate of 0.05 parts/hr and high-boiling-point components at a rate of 0.3 parts/hr and to isolate 9.4 parts of 1,7-DMN with a purity of 98% from a middle plate of the distillation column.

Isomerization Step for Isomerizing 1,7-dimethylnaphthalene with Solid Acid Catalyst (Step (3))

H mordenite having an $SiO_2/Al_2O_3$ ratio of 203 (made by Tosoh Corporation) (100 parts) and alumina sol (alumina made by Catalyst & Chemicals Ind. Co., Ltd.: 70 wt %) (20 parts) were added to deionized water, and the mixture was kneaded thoroughly. After drying at 110° C., the mixture was calcined at 500° C. for 2 hours in air and was pulverized. Particles having a diameter of 1.0 to 2.0 mm were collected as a catalyst. This catalyst (20 parts) is packed into a cylindrical stainless-steel reactor. From the bottom of the isomerization reactor, 1,7-DMN was fed at a rate of 9.4 parts/hr to carry out the isomerization reaction at 225° C. under normal pressure. The weight ratio of 1,7-DMN to 2,7-DMN in the resulting reaction solution was in the range of 2/3 to 1/1. The composition of this mixture is shown in Table 1.

Example 1

Commercially available KL zeolite ("HS-500" made by Wako Pure Chemical Industries, Ltd.; the $SiO_2/Al_2O_3$ ratio (molar ratio): 6.0) as an adsorbent was packed into a 25-mL glass column (8 mm in diameter and 500 mm in length) to prepare an adsorptive separation column. The column was heated from the exterior to keep the temperature of the packed layer at 40° C. Next, a dimethylnaphthalene isomer mixture having the composition shown in Table 1, as a stock oil, was dissolved in n-heptane as a developing solvent to prepare a 5 weight % dimethylnaphthalene solution. The solution was fed to the absorptive separation column (KL zeolite layer) at a flow rate (LHSV) to the adsorbent volume of 2.0 $h^{-1}$ for adsorption (adsorption step (A)). The solution flowing through the absorptive separation column was recovered and n-heptane was separated by distillation. As a result, 2,7-dimethylnaphthalene having a purity of 99.1% was recovered at a yield of 42% (on the basis of 2,7-dimethylnaphthalene in the stock oil, same as below) (developing solvent separation step (C)). After the adsorption operation, o-xylene as a desorption solvent was fed into the KL zeolite layer of the adsorptive separation column at a flow rate to the adsorbent volume (LHSV) of 1.0 $h^{-1}$ to desorb dimethylnaphthalenes. A dimethylnaphthalene mixture containing 37.9% 2,7-dimethylnaphthalene and 62.1% 1,7-dimethylnaphthalene was recovered (desorption step (B)).

Example 2

The experiment was carried out as in Example 1 except that n-decane was used as a developing solvent. The solution flowing through the adsorptive separation column was recovered and n-decane was separated by distillation. As a result, 2,7-dimethylnaphthalene having a purity of 97.2% was recovered at a yield of 41%.

Example 3

A stock oil (100 g) and KL zeolite (15 g) that were the same as those used in Example 1 were brought into contact in a vessel with a stirrer at 40° C. After two hours, the zeolite was removed by filtration, and n-heptane was separated by distillation. As a result, 2,7-dimethylnaphthalene having a purity of 99.2% was recovered at a yield of 40%.

Comparative Example 1

The experiment was carried out as in Example 1 except that NaY zeolite ("HS-320" made by Wako Pure Chemical Industries, Ltd.; the $SiO_2/Al_2O_3$ ratio (molar ratio): 5.5) was used as an adsorbent. No selective adsorption of 1,7-dimethylnaphthalene was observed, and almost total amounts of 1,7-dimethylnaphthalene and 2,7-dimethylnaphthalene were adsorbed. The solution flowing through the adsorptive separation column was recovered. The solution contained dimethylnaphthalenes (56% 2,7-dimethylnaphthalene and 44% 1,7-dimethylnaphthalene) in an amount corresponding to 1% of the total amount of 1,7-dimethylnaphthalene and 2,7-dimethylnaphthalene in the stock oil.

Comparative Example 2

The experiment was carried out as in Example 1 except that ZSM-5 protonic zeolite (made by N.E. CHEMCAT; the $SiO_2/Al_2O_3$ ratio (molar ratio): 26) was used as an adsorbent. No selective adsorption of 1,7-dimethylnaphthalene was observed, and 1,7-dimethylnaphthalene or 2,7-dimethylnaphthalene was not substantially adsorbed. The solution flowing through the adsorptive separation column was recovered. The solution contained dimethylnaphthalenes (59% 2,7-dimethylnaphthalene and 41% 1,7-dimethylnaphthalene) in an amount corresponding to 94% of the total amount of 1,7-dimethylnaphthalene and 2,7-dimethylnaphthalene in the stock oil.

TABLE 1

| Component | Composition (wt %) |
|---|---|
| 2,7-Dimethylnaphthalene | 55.9 |
| 1,7-Dimethylnaphthalene | 43.3 |
| Others | 0.8 |

INDUSTRIAL APPLICABILITY

According to the present invention, high-purity 2,7-dimethylnaphthalene can be efficiently isolated from a dimethylnaphthalene mixture containing 1,7-dimethylnaphthalene and 2,7-dimethylnaphthalene through a simplified process, with great industrial significance. 2,7-Naphthalene dicarboxylic acid prepared by oxidation of 2,7-dimethylnaphthalene or dimethyl 2,7-naphthalene dicarboxylate prepared by esterification of this acid are significantly useful as raw materials for high-performance polyesters having high thermal resistance and excellent physical strength.

The invention claimed is:

1. A method of purifying 2,7-dimethylnaphthalene comprising step (A) of bringing a stock oil containing a mixture of 1,7-dimethylnaphthalene and 2,7-dimethylnaphthalene and a developing solvent into contact with L zeolite to adsorb 1,7-dimethylnaphthalene on the L zeolite.

2. The method of purifying 2,7-dimethylnaphthalene according to claim 1, wherein the developing solvent is an aliphatic hydrocarbon and/or alicyclic hydrocarbon.

3. The method of purifying 2,7-dimethylnaphthalene according to claim 1, wherein the contact temperature of the stock oil and the L zeolite is in the range of 10 to 200° C.

4. The method of purifying 2,7-dimethylnaphthalene according to claim 1, wherein the amount on the basis of weight of the developing solvent is 1 to 200 times the total amount of dimethylnaphthalenes in the stock oil.

5. The method of purifying 2,7-dimethylnaphthalene according to claim 1, wherein the adsorption step (A) is carried out by a pseudo moving bed process.

6. The method of purifying 2,7-dimethylnaphthalene according to claim 1, further comprising a step (B) of desorbing dimethylnaphthalene by bringing a desorption solvent into contact with L zeolite on which 1,7-dimethylnaphthalene is adsorbed.

7. The method of purifying 2,7-dimethylnaphthalene according to claim 6, wherein the desorption solvent comprises an aromatic hydrocarbon.

8. The method of purifying 2,7-dimethylnaphthalene according to claim 6, wherein the adsorption step (A) and/or desorption step (B) is carried out by a pseudo moving bed process.

9. The method of purifying 2,7-dimethylnaphthalene according to claim 1, further comprising a step (C) separating the developing solvent from the recovered solution after the adsorption step (A).

10. The method of purifying 2,7-dimethylnaphthalene according to claim 1, wherein the stock oil is prepared by a stock oil production step (D) including the following steps (1) to (3):

Step (1): an alkenylation step for preparing 5-(p-tolyl)-2-pentene from p-xylene and 1,3-butadiene;

Step (2): a cyclization-dehydrogenation step for preparing 1,7-dimethylnaphthalene from 5-(p-tolyl)-2-pentene; and Step (3): an isomerization step for preparing 2,7-dimethylnaphthalene by isomerization of 1,7-dimethylnaphthalene.

11. The method of purifying 2,7-dimethylnaphthalene according to claim 6, further comprising a step (C) separating the developing solvent from the recovered solution after the adsorption step (A).

* * * * *